(12) United States Patent
DiTullio et al.

(10) Patent No.: US 6,686,199 B2
(45) Date of Patent: Feb. 3, 2004

(54) GENETIC MANIPULATION OF SPERMATOGONIA

(75) Inventors: Paul A. DiTullio, Northboro, MA (US); Karl M. Ebert, Millbury, MA (US)

(73) Assignee: Tran Xenogen, Inc., Shrewsbury, MA (US)

( * ) Notice: Subject to any disclaimer, the term of this patent is extended or adjusted under 35 U.S.C. 154(b) by 0 days.

(21) Appl. No.: 09/247,246

(22) Filed: Feb. 9, 1999

(65) Prior Publication Data

US 2003/0037348 A1 Feb. 20, 2003

Related U.S. Application Data

(60) Provisional application No. 60/073,386, filed on Feb. 9, 1998.

(51) Int. Cl.[7] .......................... C12N 15/00; C12N 15/87
(52) U.S. Cl. ...................... 435/455; 435/458; 435/461; 435/456; 800/21
(58) Field of Search ..................... 800/21, 14; 435/455, 435/456, 458, 461

(56) References Cited

U.S. PATENT DOCUMENTS

| | | | |
|---|---|---|---|
| 4,873,191 A | | 10/1989 | Wagner et al. |
| 5,439,440 A | * | 8/1995 | Hofmann ...................... 604/20 |
| 6,316,692 B1 | * | 11/2001 | Readhead ..................... 800/14 |

FOREIGN PATENT DOCUMENTS

| | | | | |
|---|---|---|---|---|
| JP | 09220039 | * | 8/1997 | .................. 800/21 |

OTHER PUBLICATIONS

Lai et al (Annual Anthology of University of Agriculture and Animal Science, PLA, Changchun, (1997), p. 58).*
Lai et al (Proc. Int. Conf. Anim. Biotechnol. (1997) Issue Suppl. 31–34).*
Blanchard et al (Biol. Reprod. (1997) 56(2): 495–500).*
Sato et al. Anim. Biotech. 5: 19–31, See entire document, especially abstract 1994.*
Lavitrano et al (Cell 2;57(5):717–23 see entire document expecially abstract Jun. 1989.*
Brinster et al Cell 59: 239–241, 1989 Oct. 1989.*
Pursel et al (Science 244 (4910): 1281–1288), entire document, see abstract 1989.*
Dassouli et al (J Mol Endocrinol 15(2): 129–141, entire document, see abstract 1995.*
Sperandio et al. Sperm–mediated DNA transfer in bovine and swine species; cattle and pig transgenic animal construction using sperm cell incubated with plasmid pSV2CAT and artificial insemination. Animal Biotechnology. vol. 7, pp. 59–77, e.g. p. 63, 1996.*
Lavitrano et al. Sperm–mediated gene transfer: Production of pigs transgenic for human regulator of complement activation. Transplantation Proceedings. vol. 29, pp. 3508–3509, see entire document Dec. 1997.*

Kim et al. The development of the method for sperm–mediated gene transfer in mouse and pig. Theriogenology. vol. 45, p. 337, entire document 1996.*
Kim et al. Development of a positive method for male stem cell–mediated gene transfer in mouse and pig. Molecular Reproduction and Development. vol. 46, pp. 515–526, e.g. p. 517, col 1 para. 3; pp. 529–522 Apr. 1997.*
Muramatsu et al. Foreign gene expression in the mouse testis by localized vivo gene transfer. Biochemical and Biophysical research Communications. vol. 233 pp. 45–49, especially Materials and Methodspage 46; Results p. 47, col 1; and Fig 2 Apr. 7.*
Muramatsu et al. In vivo electroporation: a convenient method for gene transfer to testicular cells. Animal Science and Technology. vol 67, pp. 975–982, e.g. p. 976, and Figs. 2,3 1996.*
Ogawa et al. Gene expression in blastocysts following direct injection of DNA into testis. Journal of Reproduction and Development. vol. 41 pp.379–382, see entire document 1995.*
Dutko et al. Murine cytomegalovirus infects spermatogenic cells. Proceedings of the National Academy of Sciences USA. vol 76, pp. 2988–2991, see for example abstract Jun. 1979.*
Schuder et al. Design of an ultrahigh–energy hydrogen thyratron/SCR research defibrillator. Medical Instrumentation. vol. 10 pp. 146–150, abstract only May 1976.*
Cameron. Semen collection and evaluation in the ram. The effect of method of stimulation on response to electroejaculation. Australian Veterinary Journal. vol. 53 pp. 380–383, abstract only Apr. 1977.*
Sambrook et al. In: Molecular Cloning, A Lab Manual. pp. 1.74–1.81, especially p. 1.80 1989.*
Brinster, R.L. et al., Proc. Natl. Acad. Sci. USA 82:4438–4442 (1985).
Synder, B.W., et al., Mol. Reproduction and Development 40:419–428 (1995).
Ebert, K.M. and J.P. Selgrath, in Applications in Mammalian Development, Cold Spring Harbor Laboratory Press, 1991.
Elbert, K.M. et al., Animal Biotechnology 1:145–159 (1990).
Osman, N., et al., Proc. Natl. Acad. Sci USA 94:14677–14682 (1997).

(List continued on next page.)

Primary Examiner—Dave T. Nguyen
Assistant Examiner—Richard A. Schnizer
(74) Attorney, Agent, or Firm—Ingrid A. Beattie; Mintz, Levin, Cohn, Ferris, Glovsky and Popeo. P.C.

(57) ABSTRACT

The invention features a method of delivering DNA to a spermatogonium by infusing DNA in situ into a testicle of a non-human animal and administering a condition or substance to the testicle to increase uptake of DNA by the spermatogonium.

19 Claims, 2 Drawing Sheets

OTHER PUBLICATIONS

Yamazaki, Yukiko et al. (1998) "In Vivo Gene Transfer to Mouse Spermatogenic Cells by Deoxyribonucleic Acid Injection Into Seminiferous Tubules and Subsequent Electroporation" Biology of Reproduction, vol. 59, pp. 1439–1444.

Baccetti et al. (2000) "Conclusions", *Mol. Reprod. Dev.*, vol. 56, pp. 329–330.

Brinster et al. (1994) "Germline Transmission of Donor Haplotype Following Spermatologonial Transplantation", *Proc. Natl. Acad. Sci. U.S.A.*, vol. 91, pp. 11303–11307.

Brinster et. al. (1994) "Spermatogenesis Following Male Germ–Cell Transplantation", *Proc. Natl. Acad. Sci. U.S.A.*, vol. 91, pp. 11298–11302.

Cappello et al. (2000) "hDAF Expression in Hearts of Transgenic Pigs Obtained by Sperm–Mediated Gene Transfer", *Transpl. Proc.*, vol. 32, pp. 895–896.

Hagmann, M. (1999) "Fertility Therapy May Aid Gene Transfer", *Science*, vol. 284, pp. 1098–1099.

Lai et al. (1997) "Generation of Transgenic Mice Expressing Human Tissue–type Plasminogen Activator in Mammary Glands by Transfecting Spermatogenia *In Vivo*", In Annual Anthology of University of Agriculture and Animal Science, PLA., Chagchun, p. 58.

Lavitrano et al. (1999) "Human Decay Accelerating Factor Transgenic Pigs for Xenotransplantation Obtained by Sperm–Mediated Gene Transfer", *Transpl. Proc.*, vol. 31, pp. 972–974.

Maione et al. (1998) "Sperm–Mediated Gene Transfer in Mice", *Mol. Repr. And Dev.*, vol. 50, pp. 406–409.

Ogura et al. (1998) "Develoment of Normal Mice from Meaphase I Oocytes, Fertilized with Primary Spermatocytes", *Proc. Natl. Acad. Sci. U.S.A.*, vol. 95, pp. 5611–5615.

Perry et al. (1999) "Mammalian Transgenesis by Intracytoplasmic Sperm Injection", *Science*, vol. 284, pp. 1180–1183.

Songsasen et al. (1998) "Live Mice from Cryopreserved Embryos Derived *In Vitro* with Cryopreseved Ejaculated Spermatozoa", *Lab. Anim. Sci.*, vol. 48, pp. 275–281.

* cited by examiner

GENETIC MANIPULATION OF SPERMATOGONIA

CROSS REFERENCE TO RELATED APPLICATIONS

This application claims priority from provisional patent application Ser. No. 60/073,386, filed on Feb. 9, 1998, the contents of which are hereby incorporated by reference.

BACKGROUND OF THE INVENTION

The invention relates to the production of transgenic animals.

The field of transgenics has grown rapidly since the initial experiments describing the introduction of foreign DNA into the developing zygote or embryo (Brinster, R. L. et al., Proc. Natl. Acad. Sci. USA 82:4438–4442 (1985), Wagner et al., U.S. Pat. No. 4,873,191 (1989)). Transgenic technology has been applied to both laboratory and domestic species for the study of human diseases (see, e.g., Synder, B. W., et al., Mol. Reprod. and Develop. 40:419–428 (1995)), production of pharmaceuticals in milk (see, for review article, Ebert, K. M. and J. P. Selgrath, "Changes in Domestic Livestock through Genetic Engineering" in *Applications in Mammalian Development*, Cold Spring Harbor Laboratory Press, 1991.), develop improved agricultural stock (see, e.g., Ebert, K. M. et al., Animal Biotechnology 1:145–159 (1990)) and xenotransplantation (see, e.g., Osman, N., et al., Proc. natl. Acad. Sci USA 94:14677–14682 (1997)). However, the technique is limiting in that it only allows for the addition of genetic material to the developing embryo and not the deletion or modification of the endogenous genes. In addition, the microinjection of DNA into the nucleus is an inefficient process resulting in only 1–2% transgenic offspring from embryos injected and frequently producing mosaic animals which do not have the transgene in all cells.

SUMMARY OF THE INVENTION

The invention features a method of delivering DNA to a spermatogonium by infusing DNA in situ into a testicle of a non-human animal and administering a condition or substance to the testicle to increase uptake of DNA by the spermatogonium. By "in situ" is meant in the original location in the body of the animal. Surgical exposure of the testis is not required. For example, a needle is inserted directly into testicular tissue and DNA delivered using a syringe. In some cases, the epididymis is surgically exposed at the head, and the DNA is delivered to the testes via a retrograde flush through the rete testes into the seminiferous tubules.

By "spermatogonium" is meant an unspecialized diploid germ cell which can undergo mitosis and meiosis to give rise to a sperm cell. For example, a spermatogonium is a primordial germ cell which can differentiate into a sperm cell. Preferably, the spermatogonium is located on the walls of the basal membrane of the seminiferous tubule. To increase uptake of DNA by a spermatogonium, the testicle is exposed to a condition such as passage of an electrical current through the testicle. The electrical current is applied using a defibrillator or electroejaculator. Application of an electrical current is a means to electroporate the DNA into the target cells, i.e., spermatogonia. DNA uptake may also be enhanced by administering a substance such as a lipid or phospholipid. The condition or substance is administered to testicle either simultaneously with the infusion of DNA or after the DNA has been infused. DNA is administered as naked DNA or by viral infection, e.g., packaged into a viral vector such as adenovirus, adeno-associated virus. By "naked" is meant free from any delivery vehicle that facilitates entry into the cell. For example, a naked DNA preparation is free of viral proteins or particles, DEAE-dextran, phospholipids, lipids, or calcium phosphate. The DNA contains a sequence encoding a selectable marker such as DNA encoding an antibiotic resistance gene, a cell surface antigen, or thymidine kinase. Following administration of the DNA, transformed or transfected cells are selected by administering an antibiotic, antibody-toxin complex, or chemical agent either systemically or locally to the testes to kill cells which do not express the DNA or to identify cells which express the DNA. The terms "transform" and "transfect" are used interchangeably throughout the specification; these terms refer to means of transferring or delivering DNA to a cell. A "transfected" or "transformed" cell is one that contains the DNA sought to be delivered to it. The DNA may also contain a second promoter which directs expression of an apoptotic gene to selectively kill germ cells which have not undergone homologous recombination with the administered DNA The DNA is administered in a volume of solution sufficient to infuse the entire testicle, e.g., 0.1 ml per testicle/per treatment for a newborn animal and up to 5 ml per testicle/per treatment for an adult animal. Repeated treatments may be carried out if desired, e.g, to increase DNA uptake.

Preferably, the non-human animal is a sheep, goat, pig, cow, chicken, rabbit, rat, mouse, or guinea pig. More preferably, the animal is prepubetal, e.g., at an age at which the testicle has not yet begun to produce sperm. For example, the preferred age of a pig is at least 30 days but not greater than 100 days. At this age, the number of target cells, i.e., spermatogonia, is relatively low. An advantage of this approach is that destruction of spermatogenic cells prior to administration of DNA is not required.

Also within the invention is a method of making a non-human transgenic animal comprising by infusing DNA in situ into a testicle of a prepubetal non-human animal, harvesting sperm cells from the animal, contacting an ovum with said the cells under conditions suitable for fertilization, and producing a non-human transgenic animal. By "transgenic non-human animal" is meant an animal that has gained (or lost) a DNA sequence from the introduction of an exogenous DNA sequence, i.e., transgene, into its own cells, or into an ancestor's germ line. Such animals are produced by natural breeding, artificial insemination, or in vitro sperm injection into ova. By the term "transgene" is meant any exogenous DNA sequence which is introduced into both the somatic and germ cells or only some of the somatic cells of a mammal. The transgene may or may not be an integral part of a chromosome. If the transgene is integrated into a chromosome, it may or may not be located at the same site as its corresponding endogenous gene sequence.

The transgene is preferably driven by a tissue specific promoter. For example, for protein expression in mammary glands, the human lactoferrin promoter is operably linked to DNA encoding a desired protein or polypeptide. Other promoters which direct preferential expression of a polypeptide in mammary gland tissue include the casein promoters (e.g., goat beta casein promoter and alpha S1 casein promoter) and whey protein promoters (e.g., whey acid protein promoter, beta lactoglobulin promoter, and alpha lactalbumin promoter). The promoter is inducible or constitutive.

Organs from transgenic animals produced according to the invention are useful for xenotransplantation. For example, the transgenic non-human animal the organs of which are suitable for transplantation into human recipients expresses human CD59 and/or lacks expression of porcine CD59 (a CD59 "knockout" pig) or the animal expresses human H-transferase and/or lacks porcine Gal($\alpha$1,3) galactosyl transferase.

The methods of the invention solve many ongoing problems in DNA delivery for the generation of transgenic animals. For example, an adenovirus genome can only carry a transgene of limited size. The use of sperm does not limit the transgene size. For example, DNA as small as a few base pairs (bp) and as large as 100–200 kilobases (kb) are delivered using the methods of the invention. Typically, approximately 5 kb, 10 kb, 20 kb or 25 kb are delivered to target cells. However, up to 400 kb may be transferred to cells. For example, more than one vector or DNA fragment is transfected simultaneously to allow for the production of multimeric proteins (i.e., immunoglobulins, FAb fragments, fibrinogen, and collagen) or expression of more than one protein coding sequence.

Other features and advantages of the invention will be apparent from the following description of the preferred embodiments thereof, and from the claims.

DETAILED DESCRIPTION

Transgenic animals made using the methods described herein are used for xenotranplantation, pharmaceutical production, protein production, and the study of human diseases.

The efficiency and reliability of the production of the transgenic animals is enhanced by the claimed methods which involve direct transfection of the stem/progenitor cells of the male testes with DNA. Following DNA delivery, semen is collected, tested for the presence of the transgene, and any animals with the transgene present in their sperm are bred to females to produce transgenic offspring. This invention has several advantages over the conventional microinjection approach in that a single experiment could produce multiple transgenic lines, no mosaic animals would be generated, the anesthetic and surgical procedures are less complex and invasive, and the need for multiple surgeries is eliminated.

For example, the method is carried out as follows. A male animal is anesthetized with a suitable anesthetic to achieve a 30–60 minute time period to complete the procedure (suitable anesthetics are known in the art, e.g., goats, valium/ketamine; rabbits, acepromazine/rompun; pigs, telazol/rompun). The optimum age for the male is prepubetal to reduce the number of target cells (e.g., stem/progenitor cells) to be transfected. However, the procedure is also useful for DNA delivery to spermatogonia of adult or mature animals. Once the animal has been anesthetized, DNA is introduced into the testes using a small gauge needle. The volume of DNA and concentration varies depending on the size of the testes and the efficiency of transfection. The transfection of the DNA is achieved using a variety of standard techniques and DNA formulations. For example, the DNA is infused in complex with lipids, other compounds known to enhance transfection, or uncompleted (i.e., naked). If DNA is infused in sterile distilled water, it may be electroporated into the cells in vivo by passing a current across the testes using an electroejaculator, heart defibrillator, or any suitable source of electrical current. After the animal has recovered, semen is collected and analyzed for the presence of the transgene. Once the transgene has been detected, the male will be bred to females to produce transgenic offspring. The time between infusion of the DNA and breeding varies depending on such factors as the age of the animal at infusion, age of sexual maturity, and the time required for differentiation from stem/progenitor cell to sperm cell.

Direct Delivery of DNA to Sperm Cells/spermatagonia

Figure 1B:
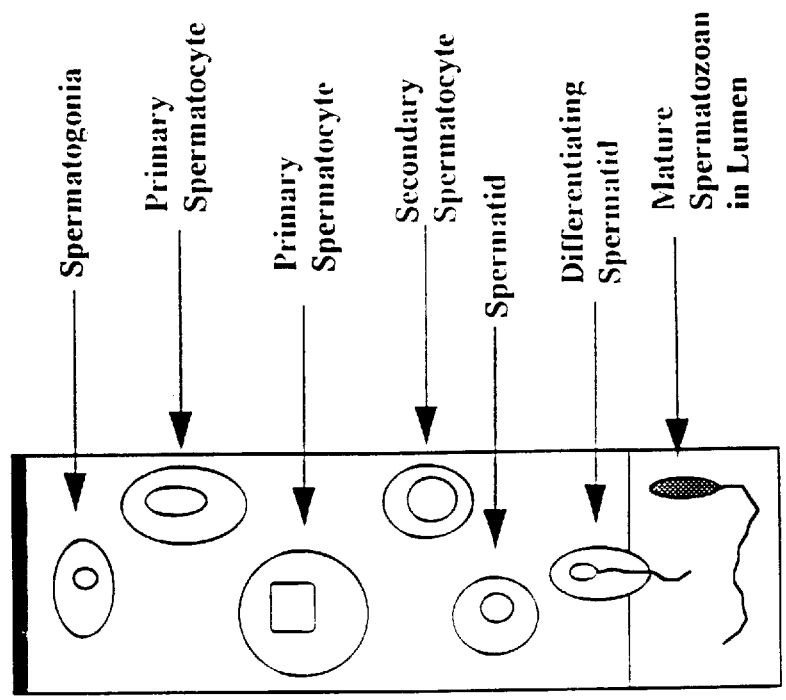
FIG. 1B is a diagram showing the organization of different cell types within the seminiferous tubules and the respective cell types.
Figure 1A:
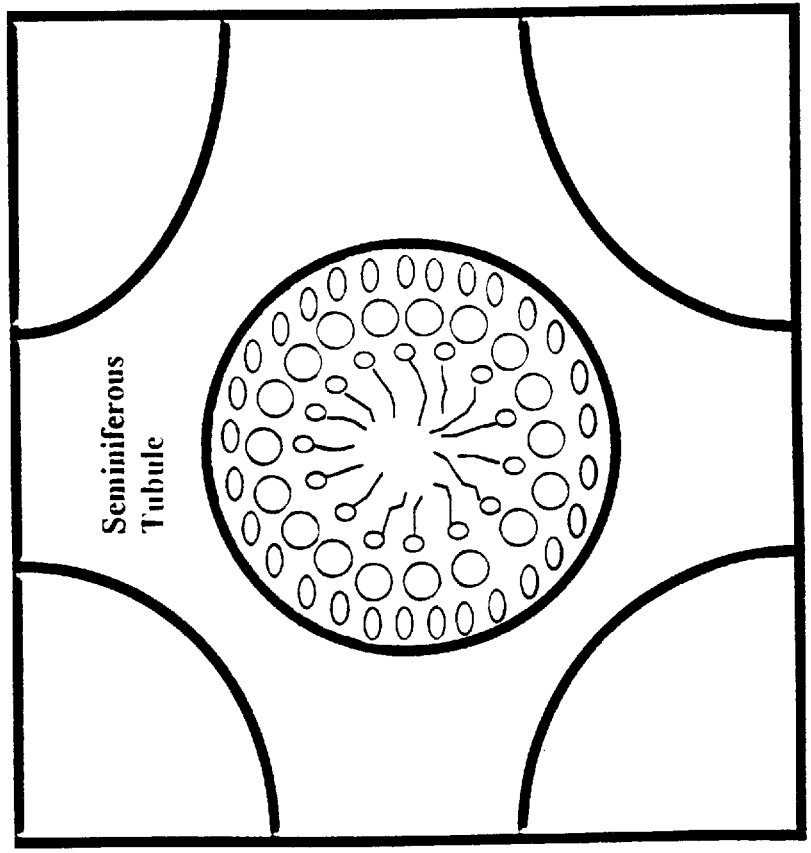
FIG. 1A is a diagram of a cross-section of a seminiferous tubule in a mammalian testes.
Figure 2:
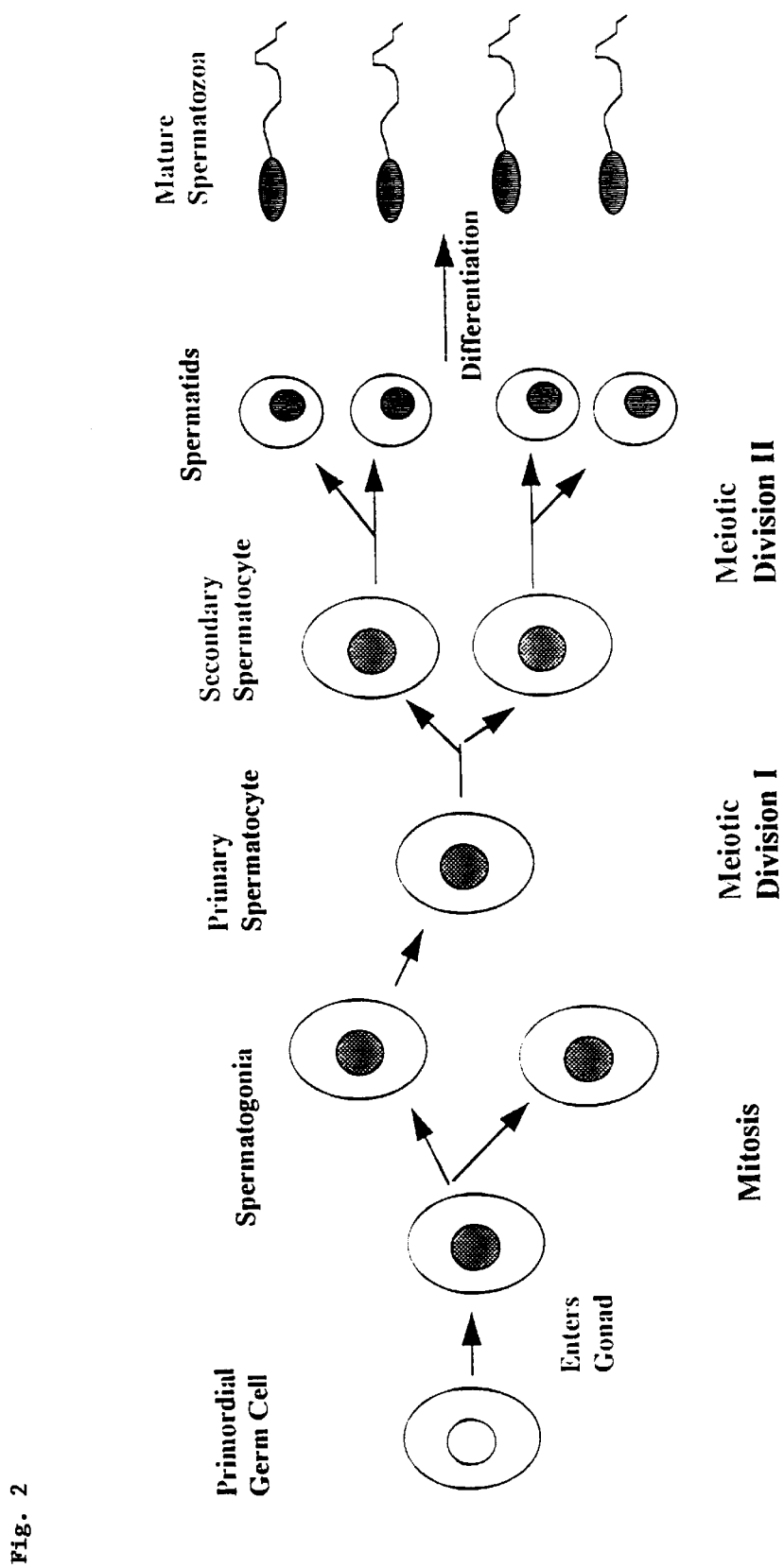
FIG. 2 is a diagram showing the stages of spermatogenesis.

The invention described herein is a method for producing a non-human transgenic animal by genetically manipulating the stem cells/spermatogonia of the male testes in vivo. The testes are composed of a series of tightly coiled tubes, termed seminiferous tubules. Testes are derived from two cell types; cells of the mesonephros region form the structural cells and the primordial germ cells give rise to the spermatogonia (FIGS. 1A and B). The seminiferous tubules contain the stem cells (spermatogonia) which when properly stimulated will undergo mitosis and meiosis to form mature sperm allowing reproduction (FIG. 2). Spermatogenesis begins in puberty and continues throughout the adult life. Therefore, the spermatogonia of the male represent the only truly regenerating stem cell population in mammals, and the introduction of DNA into a spermatogonia results in a continuous production of transgenic sperm. All transgenic animals produced by this technique carry the transgene in their germline because the DNA is integrated in the sperm before fertilization. The DNA delivery method described herein is used to transfect the spermatogonia in vivo. The approach is also useful to transfect cells in vitro. For example, spermatagonia-derived cells are cultured and transfected in vitro to be used as a sources of totipotent nuclei for cloning.

DNA is delivered to a stem cell spermatogonia via the seminiferous tubules using methods known in the art. For example, a small gauge needle is inserted into testicular tissue, and DNA is infused using a small syringe. Alternatively, the testicle is exteriorized, a tube surgically attached to the head of the epididymis, and DNA infused through the tube.

The methods of the invention are not limited by any particular formulation of DNA. For example, DNA is naked or complexed with lipids, phospholipids, or other suitable compounds to facilitate DNA uptake by cells (i.e., DEAE-dextran). The DNA contains one or more sequences which target expression to a specific tissue or are non-tissue specific, aid in transgene integration into a chromosome (e.g., viral long terminal repeat (LTR) sequences), or cause the transgene to replicate episomally. Such DNA constructs are made using methods well known in the art of molecular biology. If desired, the DNA is complexed with a lipid or other suitable compounds to facilitate DNA uptake (i.e. DEAE-dextran). A virus capable of infecting mammalian cells is also a useful delivery vehicle.

Transfection efficiency is increased by passing an electrical current across the testicle with a device such as a standard human heart defibrillator or an electroejaculator such as that described in U.S. Pat. No. 4,564,024. The efficiency of DNA delivery is assayed by collection of semen from the transformed testicle. DNA is isolated from the testicle (e.g., from semen) using standard methods, and is assayed for presence of the transgene by methods known in the art, e.g., the polymerase chain reaction (PCR) with transgene specific primers. If the semen tests positive for the desired transgene, transgenic animals are produced by breeding the male to females in estrous and allowing the animals to deliver. The progeny are tested for the presence of the transgene by PCR or southern blot analysis.

The overall efficiency of the procedure is dependent on the method of gene delivery but can be increased in several ways such as 1) subjecting the testicle to multiple rounds of transfection with the DNA vector, or 2) adding a selectable marker, e.g., an antibiotic resistance gene, to the DNA vector and infusing the testicle with the antibiotic or drug following transfection to select for the transgenic cells.

EXAMPLE 1

Timing of Testes Transfection

Experiments were carried out to determine the optimal age of animal at which in situ DNA delivery to the testes is most efficient. As a male animal matures, the testes increase in size. The increase in size corresponds to an increase in the number of target cells and primordial germ cells/spermatogonia. As a result, partial sterilization may be required prior to DNA delivery to mature animals.

According to the invention, the testes are transfected at an age when the seminiferous tubules are open to allow the DNA access to the spermatogonia but before the testes begin to actively produce sperm by meiosis. Since different species mature at different rates, this age varies among species. The optimal age for any given species is determined using known methods, e.g, monitoring a maturing animal for the onset of sperm production or histologically examining the testes from newborn to adult. Once the preferred age for DNA delivery is determined for a given species, this process need not be repeated for each individual to be treated.

The optimal time for transfecting the testicles of a Yorkshire boar was determined. Development of the testes from birth to over one year of age was monitored by collecting semen and histologically examining fixed tissue sections of testes. A gilt in heat was used to stimulate the boar. Semen was first detected between 4 and 5 months of age. Analysis of the semen revealed that the sperm count was low compared to a fully mature boar. These data indicated that the testes were still undergoing mitosis to increase cell number as well as meiosis to produce sperm.

Gross anatomical examination of the testicles indicated that the testicles increased in size from 5–7 cm to over 14 cm between 5 and 18 months of age. Tissue sections from a newborn (10–30 days old) to an adult (over 12 months) were histologically examined. In the newborn, the testicle was 1–2 cm in length, and the seminiferous tubules were only populated by germ cells. Attempts to infuse the testicles with tracking dye indicated that the seminiferous tubules were not completely open to allow flow of dye throughout the testicle. Histological examination of testicles harvested from boars between 80–100 days of ages indicated that the seminiferous tubules are open and showed an increase in the number of cells (e.g., spermatogonia) lining the tubule. At this age, the seminiferous tubules allowed transport of the tracking dye. These data indicate that DNA can successfully be delivered throughout the testicle via the seminiferous tubules after the age at which the tubules have matured to be open.

In an adult boar, histological examination of tissue sections revealed a hierarchy of cells lining the tubules with motile sperm being produced in the lumen. The seminiferous tubules of the adult animal also successfully carried tracking dye. However, the larger size of the testicle at the adult stage may reduce efficiency of DNA delivery and transfection.

These data indicate that the preferred age for DNA delivery and transfection of the testicle of a Yorkshire boar is between 30 and 100 days of age.

EXAMPLE 2

Transfection of Testes

The method described below is applicable to all species which reproduce through the production of sperm, for example but not limited to mice, rats, rabbits, pigs, goats, sheep and cows. DNA is delivered to the area surrounding the spermatogonia by utilizing the seminiferous tubules as conduits to transport the genetic material throughout the testes.

To increase overall efficiency of DNA delivery, prepubetal animals are used (thereby reducing the number of target cells in the testes to be transfected). Use of non-viral DNA is preferable because this approach removes any size limitation on the vector. The protocol described herein is useful for any DNA formulation (i.e., for either naked DNA or DNA in complex with compounds such as lipids or DEAE-dextran). Alternatively, a virus suitable to infect target cells of the testes (stem cells) is also a useful vehicle to deliver DNA to the target cells.

The resulting phenotype of the animal produced by a transformed sperm is dependent on the type of the DNA introduced and is not dependent on the method being described. Introduction of a vector or transgene containing mammary gland-specific regulatory elements directs expression of the desired protein in the animal's milk whereas a liver-specific promoter would target the blood. For example, the following tissue-specific promoters are used to direct preferential expression of DNA in mammary gland tissue: goat beta casein promoter (Ebert et al., 1994, Bio/Technology 9:669–702), alpha S1 casein promoter (Meade et al., 1990, Bio/Technology 8:443–446), whey acid protein promoter (Ebert et al., 1991, Bio/Technology 9:835–838), beta lactoglobulin promoter (Wright et al., Bio/Technology 9:830–834). The transcription of a transgene is preferably under the control of a promoter sequence different from the promoter sequence controlling the transcription of the endogenous coding sequence, e.g., a heterologous promoter. A promoter includes a cis-acting DNA sequence which is capable of directing the transcription of a gene in the appropriate tissue environment and in response to physiological regulators. Regardless of the vector or virus system being used, this method provides an efficient method to genetically manipulate the stem cells of the testes to produce transgenic animals.

The methods of the invention are useful to delivery DNA to large mammals, e.g, pigs, goats, cows, and sheep. A prepubetal male pig between 1 and 2 months of age is anesthetized with a mixture of telazol and rompun. Once the pig is under anesthesia, it is placed on a surgical table, and the area around the testes is cleaned and sterilized with alternating washes of betadine and 70% alcohol. The DNA, which has been drawn up into a 3 cc syringe with a 20 gauge needle, is infused into the testes by inserting the needle through the skin and into the organ. As the solution is infused, the needle is slowly pulled out to ensure that the entire testicle is covered. Once the DNA is infused in to the testicle, an electrical current is passed across the testicle with a human heart defibrillator that has been modified to accommodate the size of the organ. Following the transfection, the pig is allowed to recover from anesthesia and housed until it reaches maturity at approximately 5 months of age. Semen is collected from the pig for analysis. The sperm are recovered from the semen by centrifugation, washed with phosphate buffered saline, and DNA isolated by digestion with protease followed by phenol extraction and ethanol precipitation. The DNA isolated from the sperm is analyzed for the presence of the transgene by the PCR with primers specific for the transgene. Successful "knockout" of DNA sequences is also evaluated using PCR or other techniques known in the art.

If the sperm DNA tests positive for the gene of interest, transgenic animals are produced by breeding the pig to sows in heat, using the semen for artificial insemination, or doing in vitro fertilization with the sperm. The recipient females are allowed to farrow and the progeny tested for the presence of the transgene (or knockout) with DNA isolated from ear tissue or blood by the polymerase chain reaction.

Other embodiments are within the following claims

What is claimed is:

1. A method of delivering a DNA to a spermatogonium, comprising infusing in situ said DNA into a testicle of a prepubertal non-human mammal and administering an electrical current to said testicle to facilitate uptake of said DNA by said spermatogonium, wherein said DNA is infused into said testicle before production of sperm by meiosis in said testicle.

2. The method of claim 1, wherein said electrical current is applied to said testicle using a defibrillator.

3. The method of claim 1, wherein said electrical current is applied to said testicle using an electroejaculator.

4. The method of claim 1, wherein said DNA is infused in a volume of at least 0.1 ml per testicle.

5. The method of claim 1, wherein said non-human mammal is selected from the group consisting of a sheep, goat, pig, bull, rabbit, rat, mouse, and guinea pig.

6. The method of claim 5, wherein the mammal is a pig.

7. The method of claim 1, wherein said DNA comprises a selectable marker selected from the group consisting of antibiotic resistance gene, and a cell surface antigen.

8. The method of claim 1, wherein DNA is administered to said testicle before the time at which sperm can be detected.

9. The method of claim 5, wherein the age of said pig is at least 30 days.

10. The method of claim 9, wherein the age of said pig is not greater than 100 days.

11. The method of claim 1, wherein said DNA is naked.

12. A method of making a non-human transgenic animal comprising infusing in situ DNA into a testicle of a prepubertal non-human mammal, harvesting sperm cells from said mammal, contacting an ovum with said sperm cells under conditions suitable for fertilization to produce said nonhuman transgenic mammal.

13. The method of claim 12, wherein said prepubertal non-human mammal is a pig.

14. The method of claim 12, wherein said pig is at least 30 days but not greater than 100 days of age.

15. A method of delivering a DNA to a spermatogonium, comprising infusing in situ said DNA into a testicle of a prepubertal non-human mammal and administering a lipid or phospholipid to said testicle to facilitate uptake of said DNA by said spermatogonium, wherein said DNA is infused into said testicle before production of sperm by meiosis in said testicle.

16. A method of delivering a DNA to a spermatogonium, comprising infusing said DNA directly into a testicle of a prepubertal non-human mammal, wherein said DNA is packaged into a viral vector and is infused into said testicle before production of sperm by meiosis in said testicle.

17. A method of delivering a naked DNA to a spermatogonium, comprising infusing in situ said naked DNA into a testicle of a prepubertal non-human mammal, wherein said naked DNA is infused into said testicle before production of sperm by meiosis in said testicle.

18. A method of delivering a DNA to a spermatogonium, comprising infusing in situ said DNA into a testicle of a prepubertal non-human mammal and administering DEAE-dextran to said testicle to facilitate uptake of said DNA by said spermatogonium, wherein said DNA is infused into said testicle before production of sperm by meiosis in said testicle.

19. A method of delivering a DNA to a spermatogonium, comprising infusing in situ said DNA into a testicle of a non-human mammal and administering an electrical current to said testicle to facilitate uptake of said DNA by said spermatogonium, wherein said DNA is infused into said testicle before production of sperm by meiosis in said testicle and wherein said method does not comprise destruction of spermatogenic cells in said animal prior to infusing said DNA into said testicle.

* * * * *